(12) United States Patent
Hong et al.

(10) Patent No.: US 8,345,248 B2
(45) Date of Patent: Jan. 1, 2013

(54) OPTICAL CAVITY ENHANCED TURBIDIMETER AND TURBIDITY MEASURING METHOD

(75) Inventors: Jong-Cheol Hong, Daejeon (KR); Gun Yong Sung, Daejeon (KR); Sun-Hee Park, Daejeon (KR); Kyung-Hyun Kim, Daejeon (KR); Chul Huh, Daejeon (KR); Hyun-Sung Ko, Daejeon (KR); Wan-Joong Kim, Goyang (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 265 days.

(21) Appl. No.: 12/808,237

(22) PCT Filed: Jul. 29, 2008

(86) PCT No.: PCT/KR2008/004413
§ 371 (c)(1),
(2), (4) Date: Jun. 15, 2010

(87) PCT Pub. No.: WO2009/078533
PCT Pub. Date: Jun. 25, 2009

(65) Prior Publication Data
US 2010/0296095 A1   Nov. 25, 2010

(30) Foreign Application Priority Data
Dec. 17, 2007 (KR) .................. 10-2007-0132729

(51) Int. Cl.
*G01N 21/00* (2006.01)
(52) U.S. Cl. ..................................................... 356/436
(58) Field of Classification Search .................. None
See application file for complete search history.

(56) References Cited

U.S. PATENT DOCUMENTS

| | | | | |
|---|---|---|---|---|
| 4,602,243 | A * | 7/1986 | Von Bargen et al. | 341/123 |
| 6,172,824 | B1 | 1/2001 | Lehmann et al. | |
| 6,894,778 | B2 | 5/2005 | Palumbo et al. | |
| 7,113,286 | B2 * | 9/2006 | Yan | 356/436 |
| 7,277,177 | B2 | 10/2007 | Augustine et al. | |
| 2006/0232779 | A1 | 10/2006 | Shaw | |

FOREIGN PATENT DOCUMENTS
JP    2003-057230 A    2/2003

OTHER PUBLICATIONS
International Search Report for PCT/KR2008/004413 filed Jul. 29, 2008.
Written Opinion of the International Searching Authority for PCT/KR2008/004413 filed Jul. 29, 2008.

* cited by examiner

*Primary Examiner* — Gregory J Toatley
*Assistant Examiner* — Amanda Merlino

(57) ABSTRACT

Provided are an optical cavity enhanced turbidimeter and a turbidity measure method. After casting a pulse beam or a beam having a steep intensity gradient into an optical cavity, the turbidity of the inside region of the optical cavity can be calculated using an attenuation rate of an output beam from the optical cavity.

10 Claims, 2 Drawing Sheets

OPTICAL CAVITY ENHANCED TURBIDIMETER AND TURBIDITY MEASURING METHOD

TECHNICAL FIELD

The present invention relates to an optical cavity enhanced turbidimeter and a turbidity measuring method, and more particularly, to a method of measuring turbidity using an optical cavity including two highly reflective mirrors disposed to face each other so as to compare an attenuation rate of a beam output from the optical cavity with an input beam having a pulse profile or steep intensity gradient.

The present invention has been derived from a research conducted for information technology (IT) development as supported by the Ministry of Information and Communication and Institute for Information Technology Advancement, Republic of Korea (Project management No.:2006-S-007-02, Project title: ubiquitous-healthcare module system).

BACKGROUND ART

Turbidity is an optical property of fluids, and is proportional to the amount of particles that are suspended in the fluid to scatter light passing through the fluid.

For example, in environmental tests such as water examination and clinical tests such as a test using immune turbidity, it is necessary to measure the turbidity of liquids.

For instance, in a clinical test, antigens can be detected from a sample solution by measuring variations of the turbidity of the solution since the turbidity of the solution increases due to antigen-antibody reactions.

Turbidity can be measured using a turbidimeter (also, called a nephelometer) that casts one or more laser beams or white light beams through a vessel containing liquid and measures the intensities of the beams transmitted through the vessel or scattered by the liquid. In this way, the turbidimeter can measure the turbidity of the liquid.

When the turbidimeter uses at least two beams, the turbidimeter can measure turbidity more precisely with a low influence of noise, by comparing the intensities of transmitted or scattered beams.

The arrangement of the optical components of the turbidimeter can be adjusted to reduce optical noise caused by light reflected or scattered from a vessel wall or other optical components to an optical detector.

In such a turbidimeter, a laser or white light beam emitted from an optical system passes just once through a vessel containing a test solution.

That is, since a scattering of the beam is measured while the beam passes through the solution once, it is difficult to measure the turbidity of the solution when the amount of the solution is not sufficiently large or the particle concentration of the solution is low.

DISCLOSURE OF INVENTION

Technical Problem

Therefore, although turbidity measure methods such as turbidimetric immunoassay are simple, such turbidity measure methods are not suitable in fields such as medical application fields where a small amount of a sample solution is used or the concentration of a target substance in a sample solution is low.

Technical Solution

The present invention provides a method of measuring the turbidity of a sample solution by disposing the sample solution between two mirrors of an optical cavity, allowing a beam having a pulse profile or steep intensity gradient to pass through the sample solution two or more times, and measuring the attenuation rate of the beam output from the optical cavity by using an optical detector.

ADVANTAGEOUS EFFECTS

According to the optical cavity enhanced turbidimeter of the present invention, the turbidity of a sample solution can be precisely measured by disposing the vessel containing the sample solution within the optical cavity, and measuring the attenuation rate of a beam having a pulse profile or steep intensity gradient after the beam is transmitted through the optical cavity. Therefore, although a small amount of a sample solution is used, the turbidity of the sample solution can be precisely measured.

DESCRIPTION OF DRAWINGS

The above and other features and advantages of the present invention will become more apparent by describing in detail exemplary embodiments thereof with reference to the attached drawings in which.

BEST MODE

According to an aspect of the present invention, there is provided an optical cavity enhanced turbidimeter comprising: an optical source emitting a beam having a predetermined wavelength; a vessel configured to contain a liquid sample; an optical cavity comprising highly reflective mirrors facing each other to allow a beam emitted from the optical source to pass through the liquid sample repeatedly; an optical detector measuring an intensity of a beam output from the optical cavity after the beam passes through the liquid sample repeatedly; a controller calculating an attenuation rate of a beam repeatedly transmitted through the liquid sample by using measurement results of the optical detector and comparing the attenuation rate with an attenuation rate calculated when the vessel is empty so as to calculate turbidity of the liquid sample.

According to an aspect of the present invention, there is provided a method of measuring turbidity using an optical cavity, the method comprising: emitting a beam having a predetermined wavelength; inputting the beam to a side of an optical cavity comprising highly reflective mirrors; repeatedly transmitting the beam through a liquid sample contained in a vessel by repeatedly reflecting the beam between both sides of the optical cavity; outputting the beam through the other side of the optical cavity; measuring an intensity of the beam output from the optical cavity; and calculating an attenuation rate of the beam using the measured intensity of the beam and comparing the attenuation rate with an attenuation rate calculated when the vessel is empty so as to calculate and evaluate turbidity of the liquid sample.

MODE FOR INVENTION

The present invention will now be described more fully with reference to the accompanying drawings, in which exemplary embodiments of the invention are shown.

Figure 1:
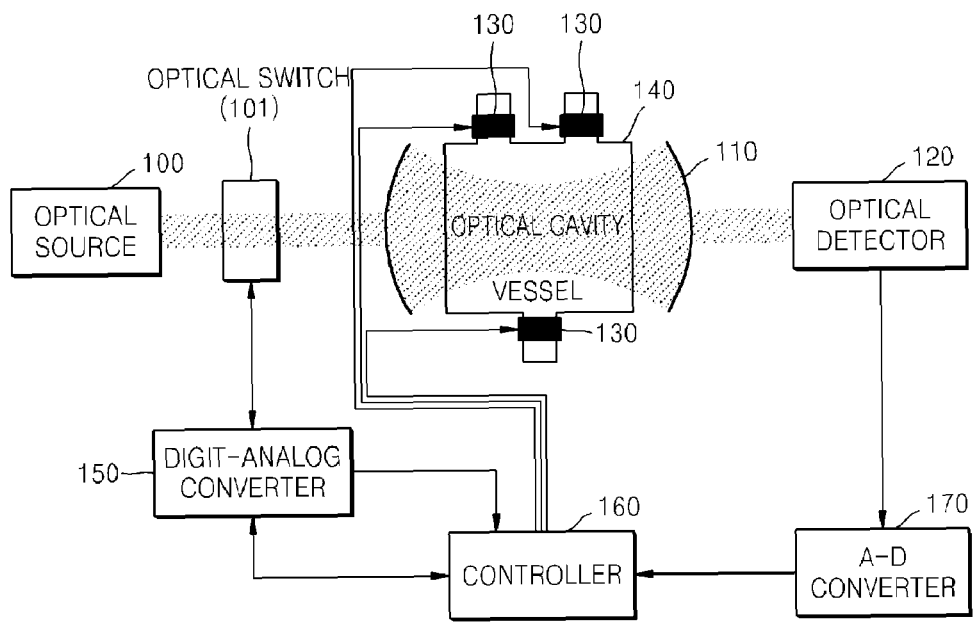
FIG. 1 illustrates an optical cavity enhanced turbidimeter according to an embodiment of the present invention.

FIG. 1 illustrates an optical cavity enhanced turbidimeter according to an embodiment of the present invention.

Referring to FIG. 1, an optical source 100 may include a component emitting white light and a filter transmitting light having a specific wavelength. Alternatively, the optical source 100 can be a laser.

An optical switch 101 controls white light or laser light emitted from the optical source 100. The optical switch 101 operates based on optical switching effects such as an electro-optic effect or an acousto-optic effect so as to vary the intensity of light emitted from the optical source 100 by converting the light into pulse light or suddenly blocking the light.

When a pulse laser is used as the optical source 100, optical switching is possible by using the optical source 100.

An optical cavity 110 repeatedly reflects light emitted from the optical source 100, and includes two highly reflective mirrors disposed to face each other.

The optical cavity 110 is excited by white or laser light cast into the optical cavity 110 from the backside of one of the two minors.

Light cast into the optical source 100 is reflected by the two minors in turns. At this time, since the two minors do not have zero transmittance, some of the light is transmitted through the two mirrors.

When pulse light is cast into the optical cavity 110, the intensity of the transmitted light varies as a pulse shape with exponentially attenuating peaks. When light cast into to the optical cavity 110 is suddenly blocked to a zero intensity level, the intensity of transmitted light attenuates exponentially.

Such exponential attenuation of transmitted light is affected by an inner material of the optical cavity 110 that absorbs and scatters light. Therefore, the turbidity of the inner material of the optical cavity 110 can be determined by measuring the attenuation rate of the transmitted light.

This method is similar to cavity ring down spectroscopy. Specifically, the cavity ring down spectroscopy uses light having a wavelength corresponding to the absorption line of a target material to observe the absorption spectrum of the target material. However, in the current embodiment of the present invention, the turbidity of a target material is determined by measuring the scattering level of light having a wavelength not corresponding to the absorption line of the target material.

An optical detector 120 measures the intensity of light transmitted through the optical cavity 110, and has a sufficiently fast response time to measure the intensity of exponentially attenuating light.

In the embodiment shown in FIG. 1, the optical detector 120 is disposed at an outside position of the optical cavity 110 so as to measure the intensity of light transmitted through the optical cavity 110. However, the present invention is not limited thereto, and thus, the optical detector 120 can be disposed inside the optical cavity 110 to directly measure scattering light.

Thus, background noise can be reduced although the intensity of the scattering light that is measured is low.

Valves 130 are formed at a vessel 140 disposed inside the optical cavity 110, so as to control the amount of liquid inside the vessel 140.

When the optical cavity enhanced turbidimeter is used in an environmental application field for measuring the turbidity of a kind of liquid, only an inlet valve and an outlet value can be used.

When the optical cavity enhanced turbidimeter is used in a medical application field to measure the turbidity levels of sample solutions so as to detect immune reactions in the sample solutions and thus determine whether target substances are included in the sample solutions, a plurality of inlet values can be used to control the supplies of the sample solutions.

Also, a target liquid is contained in the vessel 140 that can be formed of glass or plastic having high transmittance according to a wavelength. The vessel 140 may be formed of a material resulting in minimal optical absorption, irregular reflection, and scattering.

The vessel 140 can have various shapes such as a rectangular shape, a cylindrical shape, and a spherical shape. The vessel 140 may be shaped to minimize scattering light that is incident on the optical detector 120 as optical noise.

When one optical beam is used as shown in FIG. 1, the vessel 140 can have a rectangular shape. When two or more optical beams are used, the vessel 140 can have a cylindrical or spherical shape.

A digit-analog converter 150 generates an electrical signal for controlling the optical switch 101, and a controller 160 controls the overall operation of the optical cavity enhanced turbidimeter.

After a sample solution is filled in the vessel 140, the controller 160 controls the digit-analog converter 150 to cast an optical beam having a pulse shape or a steep intensity gradient into the optical cavity 110. Then, the controller 160 receives a detector signal, providing information about the intensity of light transmitted through the optical cavity 110, from the optical detector 120 through an analog-digital converter 170. Thereafter, the controller 160 analyzes the intensity of the transmitted light using the detector signal.

That is, the turbidity of a sample solution can be measured using one optical pulse. Furthermore, variations of the turbidity of a sample solution can be measured according to time, or an average turbidity of a sample solution can be measured using a plurality of optical pulses.

The analog-digital converter 170 converts an optical intensity signal output from the optical detector 120 into a digital signal so as to transmit the digital signal to the controller 160 or other computing devices.

Figure 2:
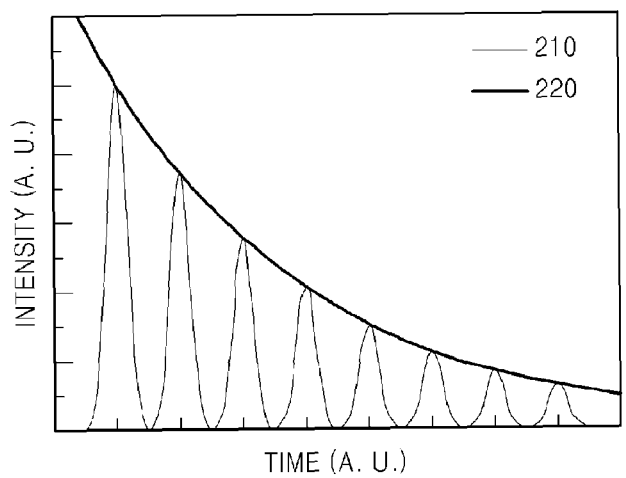
FIG. 2 illustrates an exemplary signal detected by an optical detector when an optical source emitting a pulse beam is used in an optical cavity enhanced turbidimeter, according to an embodiment of the present invention.

FIG. 2 illustrates an exemplary signal detected by an optical detector when an optical source emitting a pulse beam is used in an optical cavity enhanced turbidimeter, according to an embodiment of the present invention.

Referring to FIG. 2, a curve 210 denotes an exemplary attenuated optical signal that can be detected using the optical detector.

A pulse beam cast into an optical cavity is reflected between two mirrors of the optical cavity. During this reflection, a portion of the pulse beam is transmitted through the minor to an optical detector.

In this case, the intensity of the pulse beam inside the optical cavity is reduced due to the transmitted portion of the pulse beam. Therefore, the intensity of a portion of the pulse beam transmitted through the mirror during the next reflection is exponentially reduced.

The attenuation rate of the portions of the pulse beam transmitted through the minor is determined by the transmittance of the mirror, and light absorption and scattering (turbidity) inside the optical cavity. Therefore, the turbidity of a sample solution can be determined by comparing an attenuation rate of a beam measured when the optical cavity is empty with an attenuation rate of a beam measured when a sample solution is disposed in the optical cavity.

A curve 220 is obtained by fitting peaks of the pulses of the attenuated optical signal 210 using an exponential decrease function. The curve 220 represents the exponential attenuation rate of the pulse beam transmitted through the mirror of the optical cavity.

Figure 3:
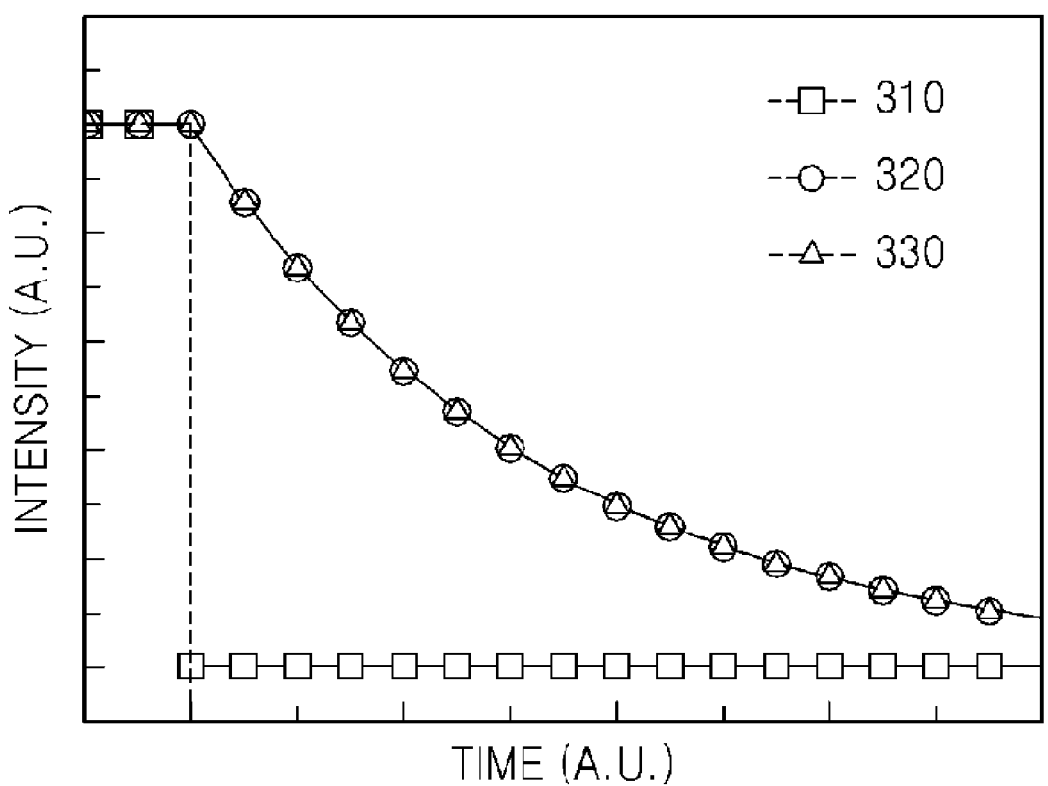
FIG. 3 illustrates an exemplary signal detected by an optical detector when an optical source emitting a beam having a steep intensity gradient is used in an optical cavity enhanced turbidimeter, according to an embodiment of the present invention.

FIG. 3 illustrates an exemplary signal detected by an optical detector when an optical source emitting a beam having a steep intensity gradient is used in an optical cavity enhanced turbidimeter, according to an embodiment of the present invention.

A curve 310 denotes an optical beam having a steep intensity gradient.

That is, the optical source of FIG. 3 is turned on and turned off for a predetermined time.

A curve 320 denotes a beam intensity signal that can be detected by an optical detector when the optical source emits an optical beam in the form of the curve 310.

Although the optical source is suddenly turned off, the beam intensity signal detected by the optical detector has an exponentially decreasing shape due to an optical cavity disposed between the optical source and the optical cavity. In the current embodiment, the attenuation rate of the optical intensity signal is also determined by the transmittance of a mirror of the optical cavity, and light-absorption and turbidity inside the optical cavity.

A curve 330 is obtained by fitting the beam intensity signal 320 using an exponential decrease function, and represents the exponential attenuation rate of the beam intensity signal 320.

The invention can also be embodied as computer-readable codes on a computer-readable recording medium. The computer-readable recording medium is any data storage device that can store data which can be thereafter read by a computer system. Examples of the computer-readable recording medium include read-only memory (ROM), random-access memory (RAM), CD-ROMs, magnetic tapes, floppy disks, optical data storage devices, and carrier waves (such as data transmission through the Internet). The computer-readable recording medium can also be distributed over network-coupled computer systems so that the computer-readable code is stored and executed in a distributed fashion.

While this invention has been particularly shown and described with reference to exemplary embodiments thereof, it will be understood by one skilled in the art that various changes in form and details may be made therein without departing from the spirit and scope of the invention as defined by the appended claims. The exemplary embodiments should be considered in descriptive sense only and not for purposes of limitation. Therefore, the scope of the invention is defined not by the detailed description of the invention but by the appended claims, and all differences within the scope will be construed as being included in the present invention.

The invention claimed is:

1. An optical cavity enhanced turbidimeter comprising:
   an optical source configured to emit a beam having a predetermined wavelength;
   a vessel having a liquid sample;
   an optical cavity containing first and second highly reflective mirrors facing each other, the vessel being disposed between the first and second mirrors, the first mirror to accept and allow the beam to repeatedly pass through the liquid sample and to the second mirror, the second mirror to accept and allow the beam to repeatedly pass through the second mirror to an optical detector;
   the optical detector configured to measure an intensity of a beam output from the optical cavity after the beam passes through the liquid sample repeatedly, where the optical detector has a sufficiently quick response time to measure the intensity of exponentially attenuating light provided by the beam output upon passing through the liquid sample;
   a controller configured to calculate an attenuation rate of the beam output, where the turbidity of the liquid sample is determined by the scattering level of light having a wavelength not corresponding to the absorption line of the target material in the liquid sample.

2. The optical cavity enhanced turbidimeter of claim 1, wherein the optical source emits a pulse beam or a beam having a steep intensity gradient.

3. The optical cavity enhanced turbidimeter of claim 1, further comprising:
   a digital-analog converter converting an intensity of a beam detected by the optical detector into a digital signal; and
   a plurality of valves controlling supply and discharge of a liquid sample to and from the vessel.

4. The optical cavity enhanced turbidimeter of claim 1, wherein the optical source is configured to emit a plurality of beams.

5. The optical cavity enhanced turbidimeter of claim 1, wherein a converter is configured to generate an electrical signal for controlling an optical switch coupled to the optical source.

6. The optical cavity enhanced turbidimeter of claim 1, wherein the vessel is formed of glass or plastic to provide minimal optical absorption and scattering of the beam.

7. A method of measuring turbidity using an optical cavity, the method comprising:
   emitting a beam having a predetermined wavelength;
   inputting the beam to a side of an optical cavity containing first and second highly reflective mirrors facing each other;
   repeatedly transmitting the beam through a liquid sample contained in a vessel by repeatedly reflecting the beam between both sides of the optical cavity using the first and second mirrors, the vessel being disposed between the first and second mirrors;
   outputting the beam through the other side of the optical cavity;
   measuring an intensity of the beam output from the optical cavity with an optical detector, the optical detector having sufficiently quick response time to measure the intensity of exponentially attenuating light provided by the beam output upon passing through the liquid sample; and calculating an attenuation rate of the beam using a controller, the controller configured to calculate the attenuation rate of the beam output, where the turbidity of the liquid sample is determined by the scattering level of light having a wavelength not corresponding to the absorption line of the target material in the liquid sample.

8. The method of claim 7, wherein the beam is a pulse beam or has a steep intensity gradient.

9. The method of claim 7 further comprising:

filling and draining the vessel with the liquid sample using at least one valve to control the amount of liquid sample inside the vessel.

10. The method of claim 7, wherein the vessel is formed of glass or plastic to provide minimal optical absorption and scattering of the beam.

* * * * *